US012590976B2

(12) United States Patent
Chen et al.

(10) Patent No.: US 12,590,976 B2
(45) Date of Patent: Mar. 31, 2026

(54) DETECTION METHOD USING BOTH FLUORESCENCE AND CHEMILUMINESCENCE LABELS

(71) Applicant: ACCESS MEDICAL SYSTEMS, LTD., Palo Alto, CA (US)

(72) Inventors: Haode Chen, Shanghai (CN); Heng Wu, Shanghai (CN); Hong Tan, San Jose, CA (US); Robert F. Zuk, Menlo Park, CA (US)

(73) Assignee: ACCESS MEDICAL SYSTEMS, LTD., Palo Alto, CA (US)

( * ) Notice: Subject to any disclaimer, the term of this patent is extended or adjusted under 35 U.S.C. 154(b) by 502 days.

(21) Appl. No.: 18/258,993

(22) PCT Filed: Dec. 21, 2021

(86) PCT No.: PCT/US2021/073053
§ 371 (c)(1),
(2) Date: Jun. 22, 2023

(87) PCT Pub. No.: WO2022/140772
PCT Pub. Date: Jun. 30, 2022

(65) Prior Publication Data
US 2024/0302386 A1    Sep. 12, 2024

Related U.S. Application Data

(60) Provisional application No. 63/129,946, filed on Dec. 23, 2020.

(51) Int. Cl.
*B01L 3/00*        (2006.01)
*B01D 15/08*      (2006.01)
(Continued)

(52) U.S. Cl.
CPC ......... *G01N 33/74* (2013.01); *G01N 21/6428* (2013.01); *G01N 21/76* (2013.01);
(Continued)

(58) Field of Classification Search
CPC .... G01N 33/74; G01N 21/6428; G01N 21/76; G01N 2021/6439; G01N 2333/585; C07K 16/26; C07K 16/44
See application file for complete search history.

(56) References Cited

U.S. PATENT DOCUMENTS

2007/0141717 A1    6/2007   Carpenter et al.
2011/0097723 A1    4/2011   Liu et al.
(Continued)

FOREIGN PATENT DOCUMENTS

WO      WO-2020206175 A1 * 10/2020    ............... B01L 3/50

*Primary Examiner* — Jennifer Wecker
*Assistant Examiner* — Oyeleye Alexander Alabi
(74) *Attorney, Agent, or Firm* — PERKINS COIE LLP; Viola T. Kung

(57)                ABSTRACT

The present invention is directed to an immunoassay method for detecting an analyte in a liquid sample; and provides accuracy and reproducibility for both high concentration and low concentration samples. The method uses both fluorescence marker and chemiluminescence marker, and reads both fluorescence signal and chemiluminescence signal. The analyte concentration is determined based on either a calibration curve for the fluorescence signal, or a calibration curve chemiluminescence signal, using a pre-established analyte concentration value.

20 Claims, 1 Drawing Sheet

(51) Int. Cl.

| | |
|---|---|
| *B01F 33/302* | (2022.01) |
| *B01F 33/3033* | (2022.01) |
| *B01L 7/00* | (2006.01) |
| *B01L 9/00* | (2006.01) |
| *B65G 47/80* | (2006.01) |
| *B82Y 20/00* | (2011.01) |
| *B82Y 30/00* | (2011.01) |
| *B82Y 40/00* | (2011.01) |
| *C12M 1/34* | (2006.01) |
| *C12M 3/06* | (2006.01) |
| *C12N 1/14* | (2006.01) |
| *C12N 1/20* | (2006.01) |
| *C12Q 1/02* | (2006.01) |
| *C12Q 1/6806* | (2018.01) |
| *C12Q 1/6844* | (2018.01) |
| *C12Q 1/6848* | (2018.01) |
| *C12Q 1/686* | (2018.01) |
| *G01N 15/10* | (2024.01) |
| *G01N 15/14* | (2024.01) |
| *G01N 15/1433* | (2024.01) |
| *G01N 21/29* | (2006.01) |
| *G01N 21/64* | (2006.01) |
| *G01N 21/65* | (2006.01) |
| *G01N 21/76* | (2006.01) |
| *G01N 30/02* | (2006.01) |
| *G01N 30/72* | (2006.01) |
| *G01N 33/543* | (2006.01) |
| *G01N 33/557* | (2006.01) |
| *G01N 33/574* | (2006.01) |
| *G01N 33/58* | (2006.01) |
| *G01N 33/74* | (2006.01) |

(52) U.S. Cl.
CPC .............. *G01N 2021/6439* (2013.01); *G01N 2333/585* (2013.01)

(56) References Cited

U.S. PATENT DOCUMENTS

| | | | |
|---|---|---|---|
| 2013/0071952 A1* | 3/2013 | Zuk | G01N 33/553 436/501 |
| 2013/0273667 A1* | 10/2013 | Zuk | G01N 33/54306 436/501 |
| 2016/0370363 A1* | 12/2016 | Tan | G01N 33/54373 |
| 2017/0052178 A1* | 2/2017 | Zuk | G01N 33/553 |
| 2018/0128826 A1 | 5/2018 | Zuk et al. | |
| 2018/0180606 A1* | 6/2018 | Zuk | G01N 33/533 |

* cited by examiner

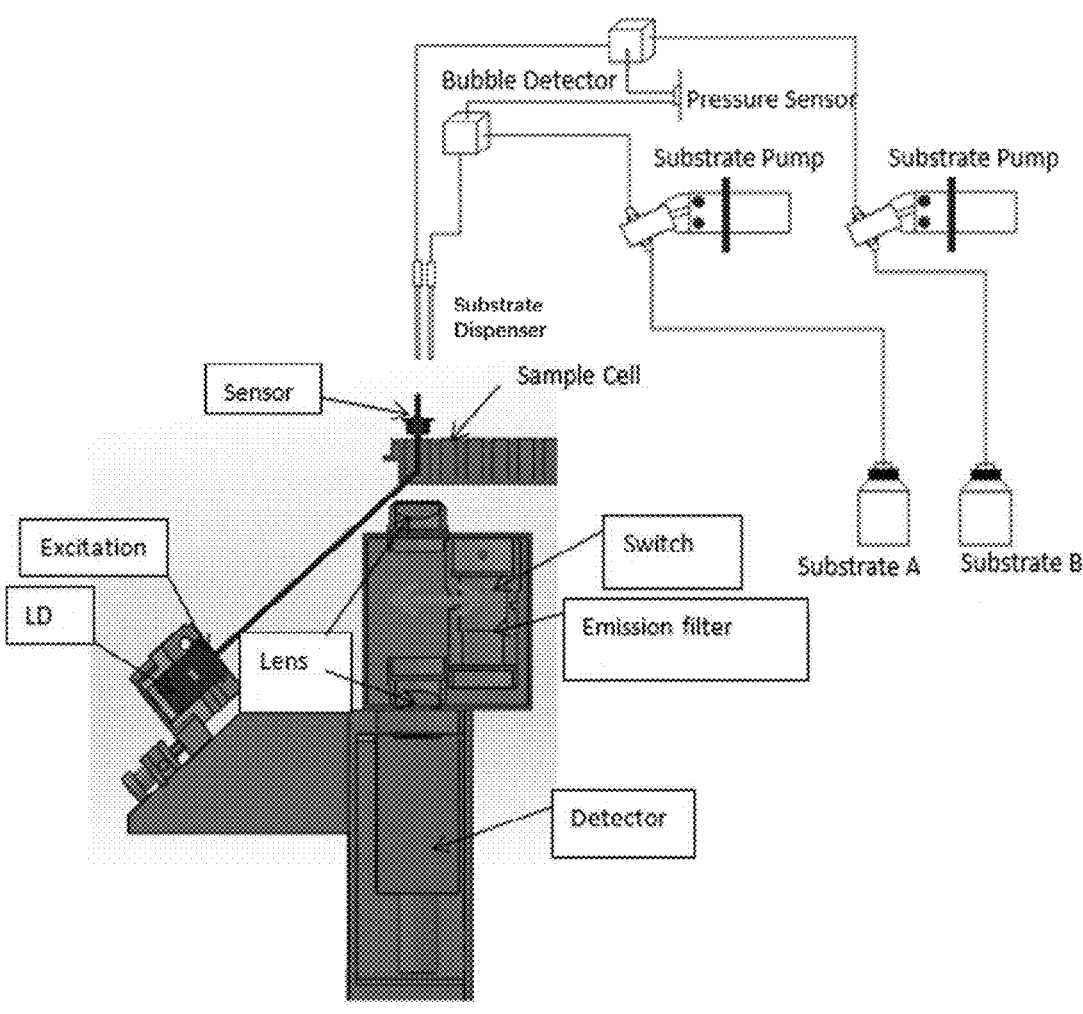

DETECTION METHOD USING BOTH FLUORESCENCE AND CHEMILUMINESCENCE LABELS

This application is a national stage of International Application PCT/US2021/073053, filed Dec. 21, 2021, which claims the priority of U.S. Provisional Application No. 63/129,946, filed Dec. 23, 2020. The contents of the above-identified applications are incorporated herein by reference in their entireties.

FIELD OF THE INVENTION

The invention relates to a method for detecting an analyte in a liquid sample using both fluorescent and chemiluminescent labels. The dual labels provide accurate quantitation on both high concentration and low concentration samples.

BACKGROUND OF THE INVENTION

Antigen antibody pairs, receptor ligand pairs, and complementary nucleic acid pairs are often used as the basis of detection in diagnostic tests. The antibodies, complementary nucleic acids or receptors fixed on a substrate to capture the target in the sample are usually called capturing molecules. After capturing molecules bind to the target analyte in the sample, detection antibodies, nucleic acids or receptors are used to detect the captured target analyte. The detection antibody, nucleic acids or receptors may have fluorescence, chemiluminescence or electrochemiluminescence labels on them to provide a signal for detection.

Among the labels, fluorescent molecules are commonly used. However, the number of target molecules in a sample varies greatly in a diagnostic detection, and their concentrations vary at least 5,000 times; for some specific targets, the concentration varies even more than 300,000 times. Although a fluorescent label can effectively detect targets with a low-end concentration, the concentration of the fluorescent label may increase by several orders of magnitude when the target concentration is high. When fluorescence molecules are close to each other, self-quenching will occur, which leads to the nonlinear relationship between the fluorescence signal and the concentration of the target, and results in inaccurate quantitation.

Chemiluminescent label requires no external radiant energy for detection. The energy comes from photons released after the chemical reaction breaks the chemical bond. However, the energy conversion efficiency of chemiluminescence labels is not 100%. A lot of energy is dissipated by heat rather than generating photons. Chemiluminescence immunoassay often shows assay variation when the analyte concentration is low.

There is still a need for improved detection methods to solve the problems encountered in immunoassay's.

BRIEF DESCRIPTION OF THE DRAWING

FIG. 1 illustrates an optical detecting system for detecting both fluorescent signal and chemiluminescent signal from the sensing surface of the probe.

DETAILED DESCRIPTION OF THE INVENTION

Definitions

Terms used in the claims and specification are to be construed in accordance with their usual meaning as understood by one skilled in the art except and as defined as set forth below.

"About," as used herein, refers to within +10% of the recited value.

An "analyte-binding molecule", as used herein, refers to any molecule capable of participating in a specific binding reaction with an analyte molecule.

An "aspect ratio" of a shape refers to the ratio of its longer dimension to its shorter dimension.

A "binding molecular," refers to a molecule that is capable to bind another molecule of interest.

A "binding pair," as used herein, refers to two molecules that are attracted to each other and specifically bind to each other. Examples of binding pairs include, but not limited to, an antigen and an antibody against the antigen, a ligand and its receptor, complementary strands of nucleic acids, biotin and avidin, biotin and streptavidin, biotin and neutravidin (a deglycosylated version of avidin), lectin and carbohydrates. Preferred binding pairs are biotin and streptavidin, biotin and avidin, biotin and neutravidin, fluorescein and anti-fluorescein, digioxigenin/anti-digioxigenin, DNP (dinitrophenol)/anti-DNP.

"Chemiluminescence," as used herein, refers to the emission of energy with limited emission of luminescence, as the result of a chemical reaction. For example, when luminol reacts with hydrogen peroxide in the presence of a suitable catalyst, it produces 3-aminophthalate in an excited state, which emits light when it decays to a lower energy level.

"Immobilized," as used herein, refers to reagents being fixed to a solid surface. When a reagent is immobilized to a solid surface, it is either be non-covalently bound or covalently bound to the surface.

A "monolithic substrate," as used herein, refers to a single piece of a solid material.

A "probe," as used herein, refers to a substrate coated with a thin-film layer of analyte-binding molecules at the sensing side. A probe has a distal end and a proximal end. The proximal end (also refers to probe tip in the application) has a sensing surface coated with a thin layer of analyte-binding molecules. Preferably, the substrate has a low fluorescence background, and the substrate can be quartz, silicon, metal, ceramic or plastic.

The present invention improves a fluorescent detection method, for example, as described in US Publication No. 2011/0312105, for measuring a concentration of an analyte. The present method uses a chemiluminescent label in addition to a fluorescent label in the method. The fluorescent detection provides sensitivity and accuracy for low concentration analytes, and the chemiluminescent detection improves the accuracy of high concentration analytes.

In the detection method of the present invention, both fluorescence and chemiluminescence labels are used. A fluorescence signal is read first to obtain the advantages of low-end sensitivity and accuracy. Then a chemiluminescence signal is read. When the fluorescence signal is high and nearly saturated, the chemiluminescence signal provides an accurate high-end concentration of the target analyte.

First Aspect

In a first aspect, the present invention is directed to a method of detecting an analyte in a liquid sample. The method comprises the steps of: (a) dipping a probe tip in a sample solution to bind an analyte, if present, to a first antibody on the probe tip, wherein the probe having a first antibody immobilized on the tip of the probe; (b) dipping the probe tip into a reagent solution comprising a biotin-conjugated second antibody to form an immunocomplex among the analyte, the first antibody, and the second antibody on the probe tip, wherein the first antibody and the second antibody are two different antibodies each against the analyte; (c)

dipping the probe tip in a wash solution; (d) dipping the probe tip into a solution comprising streptavidin labeled with a fluorescent marker and streptavidin labeled with a chemiluminescent marker; (e) dipping the probe tip in a read vessel and measuring the fluorescent signal of materials bound on the probe tip; (f) quantitate the analyte concentration based on the fluorescent signal against a first calibration curve; (g) dipping the probe tip to a triggering solution to generate a chemiluminescent signal of materials bound on the probe tip; (h) quantitate the analyte concentration based on the chemiluminescent signal against a second calibration curve, and (i) determining the analyte concentration based on either the fluorescent signal against the first calibration curve or based on the chemiluminescent signal against the second calibration curve, depending on the fluorescent signal of the analyte, using a pre-established cut-off value.

In step (a), the probe can be any shape such as rod, cylindrical, round, square, triangle, etc. In one embodiment, the probe has an aspect ratio of length to width of at least 5 to 1, or 10 to 1. A rod-shape is preferred.

The probe has a small tip for binding analytes. The tip has a smaller surface area with a diameter ≤5 mm, preferably ≤2 mm or ≤1 mm, e.g., 0.5-2 mm.

The probe tip is coated with a first antibody which binds to the analyte in a sample. Methods to immobilize reagents to the solid phase (the sensing surface of the probe tip) are common in immunochemistry and involve formation of covalent, hydrophobic or electrostatic bonds between the solid phase and reagent. The first antibody can be directly immobilized on the sensing surface. Alternatively, the first antibody can be indirectly immobilized on the sensing surface through a binding pair. For example, anti-fluorescein can be first immobilized either by adsorption to the solid surface or by covalently binding to aminopropylsilane coated on the solid surface. Then the first antibody that is labeled with fluorescein can be bound to the solid surface through the binding of fluorescein and anti-fluorescein (binding pair).

The probe tip is dipped into a sample vessel for 20 seconds to 60 minutes, preferably 20 seconds to 10 minutes, to bind the analyte to the first antibody on the probe tip. After step (a), the probe is optionally washed 1-5 times, preferably 1-3 times in a wash vessel containing a wash solution. This extra washing step may not be required because the amount of the carried-over solution is minimal due to a small binding surface area. The wash solution typically contains buffer and a surfactant such as Tween 20.

In step (b), the probe tip is dipped into a reagent vessel for 20 seconds to 10 minutes, preferably 20 seconds to 2 minutes to bind biotin-conjugated second antibody against the analyte to form an immunocomplex.

In Step (c), the probe is washed 1-5 times, preferably 1-3 times in a wash vessel containing a wash solution. The wash solution typically contains buffer and a surfactant such as Tween 20.

In step (d), two streptavidin reagents are used. i.e., streptavidin labeled with fluorescent labels and streptavidin labeled with chemiluminescent labels.

In one embodiment, each streptavidin is a monomer of streptavidin.

In another embodiment, each streptavidin reagent is further conjugated to a polymer. The polymer can be a polysaccharide (e.g., a copolymer of sucrose and epichlorohydrin (FICOLL®) or dextran), a polynucleotide, a dendrimer, a polyol, or polyethylene glycol. Polysaccharides in general exhibit negligible non-specific binding to many of the solid phase materials commonly employed in immunoassays. The polymer should have low non-specific binding, have greater than 400 or 500 kD in molecular weight to serve as an effective carrier of multiple binding streptavidins. FICOLL® is commercially available in 70K and 400K Dalton molecular weights. One preferred polymer is cross-linked FICOLL®. For example, a fluorescent streptavidin conjugate carries about 20 to 30 streptavidins per FICOLL® (2 million Daltons), and 2-3 Cy5 molecules per streptavidin. For example, a chemiluminescent streptavidin conjugate carries about 20 to 30 streptavidins per FICOLL® (2 million Daltons), and 2-3 acridinium esters molecules per streptavidin.

The size of the fluorescent label and chemiluminescent label is preferred to be small, having molecule weights ≤5000 Daltons: preferably ≤2000 Daltons: for example, 200-2000 daltons, or 300-1200 Daltons. A high molecular weight label when conjugated to streptavidin is likely to alter its biotin binding capacity and present steric hindrance.

The fluorescent label is selected from the group consisting of: cyanine, coumarin, xanthene and a derivative thereof. For example, the fluorescent dye is Cy5 (molecule weight MW 792), Alexa Fluor 647, DyLight 350 (MW 874), Dy Light 405 (MW793), DyLight 488 (MW 71011), Dy Light 550 (MW 982), Dy Light 594 (MW 1078), Dy Light 633 (MW 1066), Dy Light 650 (MW 1008), DyLight 680 (MW 950), Dy Light 755 (MW 1092), Dy Light 800 (MW 1050), an Oyster fluorescent dye, IRDye, or organic compounds comprising multiple rings chelated with a rare earth metal such as a lanthanide (Eu, Th, Sm, or Dy).

The chemiluminescent label is selected from the group consisting of: Ruthenium(II)tris-bipyridine (MW 1057), acridinium ester (9[[4-[3-[(2,5-dioxo-1-pyrrolidinyl)oxy]-3-oxopropyl]phenoxy]carbonyl]-10-methyl-acridinium trifluoromethane sulfonate, MW 632), and hemin (MW 652).

In each step (a)-(d), the reaction can be accelerated by agitating or mixing the solution in the vessel. For example, a lateral flow (orbital flow) of the solution across the probe tip can be induced, which accelerates the capture of target molecules by its binding partner immobilized to solid phase. For example, the reaction vessel can be mounted on an orbital shaker and the orbital shaker is rotated at a speed at least 50 rpm, preferably at least 200 rpm, more preferably at least 500 rpm, such as 500-1,000 rpm. Optionally, the probe tip can be moved up and down and perpendicular to the plane of the orbital flow, at a speed of 0.01 to mm/second, in order to induce additional mixing of the solution above and below the probe tip.

After step (d), the probe is washed 1-5 times, preferably 1-3 times in a wash vessel containing a wash solution, before reading the fluorescent signal (step (e)). To read a fluorescent label, the probe is placed in a clear-bottom well and read by a detector, such as those described in US 2011/0312105 (see FIG. 1 of the reference), or by the detector as shown in FIG. 1 of this application.

In step (f), the analyte concentration is quantitated against a pre-established first calibration curve for fluorescent signals.

In steps (g) and (h), a chemiluminescent signal is generated, and the analyte concentration is quantitated against a second calibration curve, which is pre-established for chemiluminescent signals. For a chemiluminescent label, the probe is placed in a clear-bottom well containing a triggering solution having a co-reactant. For example, when the chemiluminescent label is Ruthenium(II)tris-bipyridine, the co-reactant is tripropylamine.

When the chemiluminescent label is acridinium ester, the co-reactants are (a) an aqueous solution containing $HNO_3$ and $H_2O_2$ in water, and (b) an aqueous solution containing NaOH and a cationic surfactant cetyltrimethylammonium chloride (CTAC). The light emitted is measured by a photomultiplier tube (PMT).

In step (i), the analyte concentration is determined based on either the first calibration curve (fluorescent signal) or the second calibration curve (chemiluminescent signal), depending on the fluorescent signal of the analyte, using a cut-off value, which is pre-established based on a fluorescent calibration curve. In general, when the analyte concentration is low, an accurate analyte concentration is determined based on the fluorescent signal and the fluorescent calibration curve. When the analyte concentration is high, an accurate analyte concentration is determined based on the chemiluminescent signal and the chemiluminescent calibration curve. When the analyte concentration is in the middle range, whether fluorescence or chemiluminescence is used to derive analyte concentration is based on a pre-established cutoff value of the fluorescence signal. Samples with fluorescence signals below the cutoff value will have the analyte concentration determined by the fluorescence calibration. Samples with fluorescence signals above the cutoff value will have the analyte concentration determined by the chemiluminescence calibration.

In the first aspect of the invention, biotin and streptavidin can be replaced by a first member of a binding pair and a second member of binding pair. A "binding pair" is defined in the Definitions. Biotin and streptavidin are a preferred binding pair. Other useful binding pairs are biotin and avidin, biotin and neutravidin, fluorescein and anti-fluorescein, digioxigenin/anti-digioxigenin, or DNP (dinitrophenol)/anti-DNP.

In one embodiment, the method comprises the steps of: (a) dipping a probe tip in a sample solution to bind an analyte, if present, to a first antibody on the probe tip, wherein the probe having a first antibody immobilized on the tip of the probe; (b) dipping the probe tip in a reagent solution comprising a second antibody conjugated to a first member of a binding pair to form a first immunocomplex among the analyte, the first antibody, and the second antibody on the probe tip, wherein the first antibody and the second antibody are two different antibodies each against the analyte; (c) dipping the probe tip in a wash solution; (d) dipping the probe tip in a solution comprising (i) a second member of binding pair labeled with a fluorescent label and (ii) the second member of binding pair labeled with a chemiluminescent label to form a second immunocomplex with the fluorescent label and a third immunocomplex with the chemiluminescent label on the probe tip; (e) dipping the probe tip in a read vessel and measuring the fluorescent signal of the second immunocomplex bound on the probe tip; (f) quantitate the analyte concentration based on the fluorescent signal against a first calibration curve; (g) dipping the probe tip to a triggering solution to generate a chemiluminescent signal from the third immunocomplex bound on the probe tip; (h) quantitate the analyte concentration based on the chemiluminescent signal against a second calibration curve, and (i) determining the analyte concentration based on either the first calibration curve or the second calibration curve, depending on the fluorescent signal of the analyte, using a pre-established cut-off value.

Second Aspect

In a second aspect of the invention, the method steps of detection are similar to the first embodiment except (i) the probe is pre-coated with an antibody against a hapten, and (ii) a sample, a first antibody conjugated with the hapten, and a second antibody conjugated with biotin are mixed before reacting with the probe tip.

In the second aspect, the present method comprises the steps of: (a) mixing a solution comprising a sample, a first antibody conjugated with a hapten, a second antibody conjugated with biotin, wherein the first antibody and the second antibody are two different antibodies each against the analyte; (b) dipping a probe tip into the solution of (a) to form an immunocomplex among the analyte, the first antibody, and the second antibody on the probe tip; (c) dipping the probe tip in a wash solution; (d) dipping the probe tip in a solution comprising streptavidin labeled with a fluorescent label and streptavidin labeled with a chemiluminescent label; (e) dipping the probe tip in a read vessel and measuring the fluorescent signal of materials bound on the probe tip; (f) quantitate the analyte concentration based on the fluorescent signal against a first calibration curve; (g) dipping the probe tip to a triggering solution to generate a chemiluminescent signal of materials bound on the probe tip; (h) quantitate the analyte concentration based on the chemiluminescent signal against a second calibration curve, and (i) determining the analyte concentration based on either the fluorescent signal against the first calibration curve or the chemiluminescent signal against a second calibration curve, depending on the fluorescent signal of the analyte, using a pre-established cut-off value.

Steps (c)-(i) of the second aspect of the invention are identical or similar to those described in the first aspect.

In the second aspect of the invention, biotin and streptavidin can be replaced by a first member of a binding pair and a second member of binding pair, respectively. A "binding pair" is defined in the Definitions. Biotin and streptavidin are a preferred binding pair. Other useful binding pairs are biotin and avidin, biotin and neutravidin, fluorescein and anti-fluorescein, digioxigenin/anti-digioxigenin, or DNP (dinitrophenol)/anti-DNP.

In one embodiment, the method comprises the steps of: (a) mixing a solution comprising a sample, a first antibody conjugated with a hapten, a second antibody conjugated with a first member of a binding pair, wherein the first antibody and the second antibody are two different antibodies each against the analyte; (b) dipping a probe tip into the solution of (a) to form a first immunocomplex among the analyte, the first antibody, and the second antibody on the probe tip; (c) dipping the probe tip in a wash solution; (d) dipping the probe tip in a solution comprising (i) a second member of binding pair labeled with a fluorescent label and (ii) the second member of binding pair labeled with a chemiluminescent label, to form a second immunocomplex with the fluorescent label and a third immunocomplex with the chemiluminescent label on the probe tip; (e) dipping the probe tip in a read vessel and measuring the fluorescent signal of the second immunocomplex bound on the probe tip; (f) quantitate the analyte concentration based on the fluorescent signal against a first calibration curve; (g) dipping the probe tip to a triggering solution to generate a chemiluminescent signal from the second immunocomplex bound on the probe tip; (h) quantitate the analyte concentration based on the chemiluminescent signal against a second calibration curve, and (i) determining the analyte concentration based on either the first calibration curve or the second calibration curve, depending on the fluorescent signal of the analyte, using a pre-established cut-off value.

Detection Device

FIG. 1 is the structure diagram of the detection device that reads both fluorescence and chemiluminescence labels. The detection device comprises an optical module, which comprises a laser, a photon counter, a lens, a movable filter and a numerical aperture system. The fluorescent signal and chemiluminescent signal of the emitted light are detected by photomultiplier tubes (PMT). For measuring chemiluminescent signal, the laser is turned off and the filter and the numerical aperture system are removed. Then concentrated luminescence trigger A and trigger B are added into the reading cell with the substrate pump, and the chemiluminescence signal is generated.

The invention is illustrated further by the following examples that are not to be construed as limiting the invention in scope to the specific procedures described in them.

EXAMPLES

Example 1: Preparation of Probe Having Immobilized First Antibody

Quartz probes, 1 mm diameter and 2 cm in length, were coated with aminopropylsilane using a chemical vapor deposition process (Yield Engineering Systems, 1224P) following manufacturer's protocol. The probe tip was then immersed in a solution of murine monoclonal anti-fluorescein (Biospacific), 10 μg/ml in PBS (phosphate-buffered saline) at pH 7.4. After allowing the antibody to adsorb to the probe for 20 minutes, the probe tip was washed in PBS.

Example 2. Preparation of Labelled Capture Antibody and Signal Antibody

Capture antibody for procalcitonin (PCT) was a monoclonal antibody obtained from Hytest and labeled with fluorescein by standard methods. Typically, there were about 4 fluorescein substitutions per antibody.

Signal antibody for PCT was a polyclonal antibody obtained from Hytest and labelled with biotin by standard methods. Typically, there were about 4 biotins per antibody.

Example 3. Preparation of Cy5-Streptavidin

32 μL of Cy 5-NHS (GE Healthcare) at 5 mg/ml in DMF reacted with 1 ml of streptavidin (Scripps Labs) at 2.4 mg/ml in 0.1 M sodium carbonate buffer pH 9.5 for 40 minutes at 30° C. Applying the mixture to a PD 10 column (Pharmacia) removed unconjugated Cy 5. Spectral analysis indicated 2.8 Cy 5 linked per streptavidin molecule.

Example 4. Preparation of Crosslinked FICOLL® 400

To 2 ml of FICOLL® 400 (Sigma/Aldrich) that was aminated to contain 88 amines per FICOLL® 400 kD (Skold Technology) at 20 mg/ml in PBS was added 10 μL of SPDP (succinimydyl 6-[3-[2-pyridyldithio]-proprionamido] hexanoate) at 50 mg/ml in DMF (N,N-Dimethylformamide). The SPDP to FICOLL® MCR was 15. The mixture reacted for 1 hour at room temperature and followed by dialysis. Thiol incorporation was estimated to be 5.5 per FICOLL® 400 kD by standard methods.

To deprotect the thiols on SPDP-labeled FICOLL® 400, 30 μL of DTT at 38 mg/ml PBS was added to 20 mg in 1 ml PBS and allowed to react for two hours at room temperature. The SH-FICOLL® was purified on a PD10 column.

SMCC (succinimidyl 4-[N-malemidomethyl]cyclohexan-1-carboxylate) was linked to aminated FICOLL® 400 (88 amines/Ficoll) as follows: Aminated FICOLL® 400 at 10 mg in 1 ml PBS was mixed with 25 μL SMCC at 10 mg/ml DMF for a SMCC/Ficoll MCR of 30. The mixture reacted for 1 hour at room temperature and followed by purification on a PD10 column (GE Healthcare).

To crosslink the SH-FICOLL® 400 and SMCC-FICOLL® 400, 10 mg in 1 ml PBS SH-FICOLL® 400 was mixed with 10 mg in 1 ml PBS SMCC-FICOLL® 400. The mixture reacted for overnight at room temperature.

Example 5. Preparation of Acridinium Ester-Streptavidin-Crosslinked FICOLL®

To provide linking sites for subsequent streptavidin conjugation to the crosslinked FICOLL® 400 (Example 4), the residual amines were then reacted with an excess of SPDP. 20 mg of crosslinked FICOLL® 400 was mixed with 75 μL SPDP at 50 mg/ml DMF. The mixture reacted for 1 hour at room temperature followed by dialysis versus PBS. The SPDP labeled crosslinked FICOLL® 400 preparations were then purified on a Sepharose 4B CL column.

Streptavidin (SA) at 1.5 mg/ml in 1 ml PBS was mixed with 5 μL SMCC at 5 mg/ml DMF and reacted for 1 hour at room temperature followed by purification on a PD 10 column.

The thiols on crosslinked FICOLL® 400-SPDP were deprotected by adding 30 μL DTT at 38 mg/ml to 0.7 mg crosslinked FICOLL® 400-SPDP in 1 ml PBS and reacting for 1 hour at room temperature followed by a PD 10 column to purify the crosslinked FICOLL® 400-SH.

The SA-SMCC was mixed with crosslinked FICOLL® 400-SH and reacted overnight at room temperature. 10 μL NEM (N-ethyl-maleimide) at 12.5 mg/ml was then added and reacted for ½ hour at room temperature. The streptavidin-crosslinked FICOLL® conjugate was then purified on a Sepharose 4B CL column.

To link the acridinium ester (AE) to streptavidin-crosslinked FICOLL®, 4.5 ul of 9-[[[4-[(2,5-Dioxo-1-pyrrolidinyl)oxy]-4-oxobutyl][(4-methylphenyl)sulfonyl]amino]carbonyl]-10-(3-sulfopropyl)-acridinium inner salt (synonym NSP-SA-NHS, Biosynth Carbosynth) in DMF at 10 mg/ml was mixed with 3.0 ml of streptavidin-crosslinked FICOLL® at 0.3 mg/ml in PBS, pH 7.4 and allowed to react for 1 hour at room temperature. The conjugate was then purified on a PD10 column to remove unlinked AE.

Example 6. Preparation of Cy5-Streptavidin-Crosslinked FICOLL®

5.8 μL of SMCC (succinimidyl 4-[N-malemidomethyl] cyclohexan-1-carboxylate) Pierce Chemical) at 10 mg/ml in DMF reacted with 2 mg Cy5-streptavidin (Example 3) in 1 ml PBS pH 7.4 for 1 hour at room temperature. Applying the mixture to a PD 10 column removed unbound SMCC.

The thiols on crosslinked FICOLL® 400-SPDP were deprotected by adding 30 μL DTT at 38 mg/ml to 1 mg crosslinked FICOLL® 400-SPDP in 1 ml PBS and reacting for 1 hour at room temperature followed by a PD 10 column to purify the crosslinked FICOLL®.

The Cy5-streptavidin-SMCC was mixed with crosslinked FICOLL® 400-SH and reacted overnight at room temperature. 10 μL NEM (Aldrich) at 12.5 mg/ml was then added and reacted for ½ hour at room temperature. The conjugate was then purified on a Sepharose 4B CL column. It was estimated that the conjugate carried about 20 to 30 streptavidins per FICOLL® (2 million Daltons), and 2-3 Cy5s per streptavidin.

Example 7: Preparation of Ruthenium(II)tris-bipyri-dine-Streptavidin-Crosslinked FICOLL®

0.176 μg of Ruthenium(II)tris-bipyridine-NHS (Me-soScale Discovery, R91BN-2) in 35 μl dimthylformaide is mixed with 1 mg streptavidin in PBS pH 7.4 and allowed to react for one hour at room temperature. Typically about 2 to 4 Ru labels are linked per streptavidin molecule. The result-ing Ru-streptavidin conjugate is purified on a PD-10 column (Pharmacia). 2.9 μL of SMCC (Pierce Chemical) at 10 mg/ml in DMF reacted with 1 mg of Ru-streptavidin in 1 ml PBS pH 7.4 for 1 hour at room temperature. The mixture is applied to a PD 10 column to remove unbound SMCC.

The thiols on crosslinked FICOLL® 400-SPDP are deprotected by adding 30 μL DTT at 38 mg/ml to 1 mg crosslinked FICOLL® 400-SPDP in 1 ml PBS and reacting for 1 hour at room temperature followed by a PD 10 column to purify the crosslinked FICOLL®.

The Ru-streptavidin-SMCC is mixed with crosslinked FICOLL® 400-SH and reacted overnight at room tempera-ture. 10 μL NEM (Aldrich) at 12.5 mg/ml is then added and reacted for ½ hour at room temperature. The conjugate is then purified on a Sepharose 4B CL column. The resulting conjugate has about 20 streptavidins per crosslinked FICOLL® and 2-4 Ru per streptavidin.

Example 8. Assay Results

The example provides a fast detection method integrating fluorescence and chemiluminescence for detecting procal-citonin (PCT) in whole blood samples.

The probe was pre-coated with anti-fluorescein antibody conjugated to cross-linked FICOLL polymer.

4 μl of whole blood, 100 μL of 0.2 μg/mL of fluorescein-acylated mouse anti-human PCT monoclonal antibody, and 100 μL of 0.2 μg/mL of biotinylated polyclonal anti-human PCT antibody were added to the anti-fluorescein coated probe and reacted for 240 seconds.

The probe was washed with PBST (PBS-Tween), and then transferred into another well containing 100 μL of 10 μg/mL of Cy5-streptavidin-crosslinked FICOLL® and 100 μL 10 μg/mL of acridinium ester-streptavidin-crosslinked FICOLL® and reacted for 15 seconds.

The probe was washed with PBST, and then the fluores-cence signal of the probe was read by a device of FIG. 1 and quantitated against a fluorescence standard curve. Then, the probe was moved to a well containing 130 μL of trigger A and 130 μL of trigger B to generate a chemiluminescence signal. Trigger A contained 0.1M $HNO_3$ and 0.3% $H_2O_2$ in water, and the trigger B contained 0.25M NaOH and 7 mM CTAC in water. The chemiluminescence signal was also read by a device of FIG. 1, and quantitated against a chemiluminescence standard curve. The results are summa-rized in Tables 1-3.

This method detected PCT in whole blood and only took 6 minutes from addition of the sample to result reading. The analytical sensitivity was 0.01 ng/mL and the detection range was 0.01-1,000 ng/mL. Both the low-end and high-end detection signals show good linearity, as shown in the following table.

TABLE 1

Test Results of Procalcitonin Fluorescence Signals

| Concentration (ng/mL) | Fluorescence signal |
| --- | --- |
| 1000 | 140094 |
| 500 | 126928 |
| 250 | 99060 |
| 100 | 77391 |
| 33.3 | 45602 |
| 11.1 | 22443 |
| 3.7 | 8095 |
| 1.23 | 2793 |
| 0.412 | 993 |
| 0.137 | 342 |
| 0.046 | 98 |
| 0 | 19 |

TABLE 2

Test Results of the Procalcitonin Chemiluminescence Signals

| Concentration (ng/mL) | Chemiluminescence signal |
| --- | --- |
| 1000 | 96798 |
| 500 | 52051 |
| 250 | 28920 |
| 100 | 14840 |
| 33.3 | 4603 |
| 11.1 | 1796 |
| 3.7 | 695 |
| 1.23 | 267 |
| 0.412 | 109 |
| 0.137 | 79 |
| 0.046 | 89 |
| 0 | 75 |

TABLE 3

Repeatability of Test Results of Fluorescence and Luminescence Methods

| | Sample 1 | | Sample 2 | |
| CV | Fluorescence signal | Chemilu-minescence signal | Fluorescence signal | Chemilu-minescence signal |
| --- | --- | --- | --- | --- |
| 1 | 4135 | 1354 | 1117 | 232 |
| 2 | 4178 | 1284 | 1200 | 246 |
| 3 | 4165 | 1419 | 1195 | 226 |
| 4 | 4004 | 1697 | 1194 | 256 |
| 5 | 4176 | 1421 | 1209 | 213 |
| 6 | 3934 | 1437 | 1148 | 232 |
| 7 | 4056 | 1549 | 1171 | 226 |
| 8 | 4295 | 1346 | 1183 | 278 |
| 9 | 4007 | 1298 | 1122 | 243 |
| 10 | 4133 | 1401 | 1098 | 255 |
| AVE | 4108.3 | 1420.6 | 1163.7 | 240.7 |
| STD | 107.02 | 123.48 | 39.69 | 18.90 |
| CV | 2.6% | 8.7% | 3.4% | 7.9% |

The main difference between the fluorescence and chemi-luminescence systems is in different resolutions between high concentrations and low concentrations.

A resolution ratio is calculated as a ratio of the signal of one concentration vs. the signal of its immediate lower concentration. The resolution ratios are shown in Table 4.

TABLE 4

| | | | | |
|---|---|---|---|---|
| | | Resolution Ratios | | |
| Concentration (ng/mL) | Fluorescence signal | Resolution Ratio | Chemiluminescent signal | Resolution Ratio |
| 1000 | 140094 | | 96798 | |
| 500 | 126928 | 1.10 | 52051 | 1.86 |
| 250 | 99060 | 1.28 | 28920 | 1.80 |
| 100 | 77391 | 1.28 | 14840 | 1.95 |
| 33.3 | 45602 | 1.70 | 4603 | 3.22 |
| 11.1 | 22443 | 2.03 | 1796 | 2.56 |
| 3.7 | 8095 | 2.77 | 695 | 2.58 |
| 1.23 | 2793 | 2.90 | 267 | 2.60 |
| 0.412 | 993 | 2.81 | 109 | 2.45 |
| 0.137 | 342 | 2.90 | 79 | 1.38 |
| 0.046 | 98 | 3.49 | 89 | 0.89 |
| 0 | 19 | 5.16 | 75 | 1.19 |

Resolution ratio >2.0 is considered acceptable, to distinguish the low (0-1.23 ng/ml), middle (1.24-11.1 ng/ml), and high (11.2-1,000 ng/ml) concentrations.

TABLE 5

| | | | | |
|---|---|---|---|---|
| | | Precision testing of blood samples | | |
| | Fluorescence signal | Fluorescence concentration | Optical signal | Luminescence concentration |
| | | Low-concentration sample | | |
| Rep1 | 504 | 0.205 | 95 | 0.282 |
| Rep2 | 551 | 0.225 | 85 | 0.191 |
| Rep3 | 587 | 0.240 | 85 | 0.191 |
| Rep4 | 530 | 0.216 | 82 | 0.164 |
| Rep5 | 559 | 0.228 | 83 | 0.173 |
| Rep6 | 492 | 0.200 | 102 | 0.346 |
| Rep7 | 516 | 0.210 | 112 | 0.425 |
| Rep8 | 492 | 0.200 | 93 | 0.264 |
| Rep9 | 458 | 0.186 | 87 | 0.209 |
| Rep10 | 563 | 0.230 | 89 | 0.228 |
| mean | 525 | 0.214 | 91 | 0.247 |
| sd | 39.9 | 0.017 | 9.5 | 0.084 |
| CV % | 7.60% | 7.81% | 10.44% | 33.95% |

TABLE 5-continued

| | | | | |
|---|---|---|---|---|
| | | Precision testing of blood samples | | |
| | Fluorescence signal | Fluorescence concentration | Optical signal | Luminescence concentration |
| | | Medium-concentration sample | | |
| Rep1 | 6698 | 3.05 | 519 | 2.69 |
| Rep2 | 7367 | 3.36 | 557 | 2.91 |
| Rep3 | 6726 | 3.06 | 608 | 3.20 |
| Rep4 | 7112 | 3.24 | 562 | 2.94 |
| Rep5 | 6280 | 2.86 | 559 | 2.92 |
| Rep6 | 6387 | 2.91 | 560 | 2.92 |
| Rep7 | 6535 | 2.97 | 583 | 3.06 |
| Rep8 | 7166 | 3.27 | 553 | 2.89 |
| Rep9 | 6456 | 2.94 | 602 | 3.17 |
| Rep10 | 6660 | 3.03 | 538 | 2.80 |
| mean | 6739 | 3.07 | 564 | 2.95 |
| sd | 362.1 | 0.169 | 27.2 | 0.157 |
| CV % | 5.37% | 5.50% | 4.82% | 5.32% |
| | | High-concentration sample | | |
| Rep1 | 48133 | 38.6 | 7628 | 53.0 |
| Rep2 | 52347 | 47.5 | 7161 | 50.0 |
| Rep3 | 54004 | 51.0 | 6836 | 47.9 |
| Rep4 | 55234 | 53.5 | 7861 | 54.6 |
| Rep5 | 52185 | 47.1 | 6968 | 48.7 |
| Rep6 | 50647 | 43.9 | 6676 | 46.8 |
| Rep7 | 55917 | 55.0 | 7519 | 52.3 |
| Rep8 | 57420 | 58.1 | 6845 | 47.9 |
| Rep9 | 51273 | 45.2 | 6456 | 45.4 |
| Rep10 | 55065 | 53.2 | 7521 | 52.3 |
| mean | 53223 | 49.3 | 7147 | 49.9 |
| sd | 2810.9 | 5.895 | 464.1 | 3.023 |
| CV % | 5.28% | 11.95% | 6.49% | 6.06% |

Table 5 shows that fluorescent detection has high accuracy in both low and medium concentration samples, and chemiluminescent detection has high accuracy in both medium and high concentration samples.

Plasma Sample Recovery Testing Based on the Concentration Switching System:

A high-concentration sample of PCT with a known concentration is selected, which is then diluted by a negative sample for a 3-fold series dilution. Each sample is tested twice. The ratio of mean concentration and the theoretical value is calculated as the recovery rate (Table 6).

TABLE 6

| | | | | | | | | |
|---|---|---|---|---|---|---|---|---|
| | | Comparing Fluorescent Detection and Chemiluminescence Detection | | | | | | |
| ng/ml | Recovery rate of fluorescence system | | | | Recovery rate of chemiluminescence system | | | |
| Theoretical value | Measured value 1 | Measured value 2 | Measured average | Recovery rate | Measured value 1 | Measured value 2 | Measured average | Recovery rate |
| 75.3 | 85.0 | 104.4 | 94.7 | 125.78% | 78.2 | 78.2 | 78.2 | 103.86% |
| 25.1 | 37.0 | 31.7 | 34.3 | 136.80% | 23.0 | 25.5 | 24.3 | 96.76% |
| 8.37 | 8.39 | 7.98 | 8.18 | 97.81% | 7.65 | 7.98 | 7.82 | 93.43% |
| 2.79 | 2.75 | 2.68 | 2.71 | 97.31% | 2.86 | 2.40 | 2.63 | 94.23% |
| 0.930 | 0.97 | 0.91 | 0.939 | 100.99% | 0.82 | 0.98 | 0.899 | 96.74% |
| 0.310 | 0.325 | 0.316 | 0.320 | 103.38% | 0.411 | 0.342 | 0.377 | 121.52% |
| 0.103 | 0.120 | 0.090 | 0.105 | 102% | 0.134 | 0.293 | 0.213 | 206.66% |

The fluorescent and chemiluminescence results of Table 6 are selected and combined to select for best recovery rates (Table 7). In Table 7, measured average values of 0.11-8.18 are based on fluorescent signals, and measured average values of 24.3-78.2 are based on chemiluminescence signals

TABLE 7

Combining Fluorescent Detection and Chemiluminescence Detection for Quantitation

| ng/ml | Recovery results after switching between the fluorescence and chemiluminescence systems | | | |
|---|---|---|---|---|
| Theoretical value | Measured value 1 | Measured value 2 | Measured average | Recovery rate |
| 75.3 | 78.2 | 78.2 | 78.2 (Chem) | 103.86% |
| 25.1 | 23.0 | 25.5 | 24.3 (Chem) | 96.76% |
| 8.37 | 8.39 | 7.98 | 8.18 (Fluo) | 97.81% |
| 2.79 | 2.75 | 2.68 | 2.71 (Fluo) | 97.31% |
| 0.930 | 0.97 | 0.91 | 0.94 (Fluo) | 100.99% |
| 0.310 | 0.32 | 0.32 | 0.32 (Fluo) | 103.38% |
| 0.103 | 0.12 | 0.09 | 0.11 (Fluo) | 101.58% |

By combining the advantages of a low-end fluorescence system and a high-end chemiluminescence system, the recovery results in the entire concentrations are in a range of 96%-104%.

The invention, and the manner and process of making and using it, are now described in such full, clear, concise and exact terms as to enable any person skilled in the art to which it pertains, to make and use the same. It is to be understood that the foregoing describes preferred embodiments of the present invention and that modifications may be made therein without departing from the scope of the present invention as set forth in the claims. To particularly point out and distinctly claim the subject matter regarded as invention, the following claims conclude this specification.

What is claimed is:

1. A method of detecting an analyte in a liquid sample, comprising the steps of:
   (a) dipping a probe tip in a sample solution to bind an analyte, if present, to a first antibody on the probe tip, wherein the probe having a first antibody immobilized on the tip of the probe;
   (b) dipping the probe tip in a reagent solution comprising a second antibody conjugated to a first member of a binding pair to form a first immunocomplex among the analyte, the first antibody, and the second antibody on the probe tip, wherein the first antibody and the second antibody are two different antibodies each against the analyte;
   (c) dipping the probe tip in a wash solution;
   (d) dipping the probe tip in a solution comprising (i) a second member of binding pair labeled with a fluorescent label and (ii) the second member of binding pair labeled with a chemiluminescent label, to form a second immunocomplex having the fluorescent label and a third immunocomplex having the chemiluminescent label on the probe tip;
   (e) dipping the probe tip in a read vessel and measuring the fluorescent signal of the second immunocomplex bound on the probe tip;
   (f) quantitate the analyte concentration based on the fluorescent signal against a first calibration curve;
   (g) dipping the probe tip to a triggering solution to generate a chemiluminescent signal from the third immunocomplex bound on the probe tip;

(h) quantitate the analyte concentration based on the chemiluminescent signal against a second calibration curve, and
   (i) determining the analyte concentration based on either the fluorescent signal or the chemiluminescent signal.

2. A method of detecting an analyte in a liquid sample, comprising the steps of:
   (a) mixing a solution comprising a sample, a first antibody conjugated with a hapten, a second antibody conjugated with a first member of a binding pair, wherein the first antibody and the second antibody are two different antibodies each against the analyte;
   (b) dipping a probe tip into the solution of (a) to form a first immunocomplex among the analyte, the first antibody, and the second antibody on the probe tip;
   (c) dipping the probe tip in a wash solution;
   (d) dipping the probe tip in a solution comprising (i) a second member of binding pair labeled with a fluorescent label and (ii) the second member of binding pair labeled with a chemiluminescent label, to form a second immunocomplex having the fluorescent label and a third immunocomplex having the chemiluminescent label on the probe tip;
   (e) dipping the probe tip in a read vessel and measuring the fluorescent signal of the second immunocomplex bound on the probe tip;
   (f) quantitate the analyte concentration based on the fluorescent signal against a first calibration curve;
   (g) dipping the probe tip to a triggering solution to generate a chemiluminescent signal from the third immunocomplex bound on the probe tip;
   (h) quantitate the analyte concentration based on the chemiluminescent signal against a second calibration curve, and
   (i) determining the analyte concentration based on either the fluorescent signal or the chemiluminescent signal.

3. The method according to claim 1, wherein the binding pair is biotin and streptavidin, biotin and avidin, biotin and neutravidin, fluorescein and anti-fluorescein, digioxigenin/anti-digioxigenin, or DNP (dinitrophenol)/anti-DNP.

4. The method according to claim 3, wherein the first member of the binding pair is biotin, and the second member of the binding pair is streptavidin.

5. The method according to claim 1, further comprising reading the background fluorescence signal of the probe tip before step (d), wherein the fluorescent signal of step (f) is calculated by subtracting the background fluorescence signal from the fluorescence signal of step (e).

6. The method according to claim 1, wherein the probe tip surface is <about 5 mm.

7. The method according to claim 1, wherein the fluorescent label is a cyanine dye.

8. The method according to claim 1, wherein the chemiluminescent label is ruthenium (II) tris-bipyridine or an acridinium ester.

9. The method according to claim 4, wherein the streptavidin is conjugated to a copolymer of sucrose and epichlorohydrin.

10. The method according to claim 9, wherein each copolymer carries about 20 to 30 streptavidins.

11. The method according to claim 10, wherein each copolymer further carries 2-3 Cy5 molecules per streptavidin, or 2-3 acridinium esters molecules per streptavidin.

12. The method according to claim 2, wherein the binding pair is biotin and streptavidin, biotin and avidin, biotin and neutravidin, fluorescein and anti-fluorescein, digioxigenin/anti-digioxigenin, or DNP (dinitrophenol)/anti-DNP.

13. The method according to claim 12, wherein the first member of the binding pair is biotin, and the second member of the binding pair is streptavidin.

14. The method according to claim 2, further comprising reading the background fluorescence signal of the probe tip before step (d), wherein the fluorescent signal of step (f) is calculated by subtracting the background fluorescence signal from the fluorescence signal of step (e).

15. The method according to claim 2, wherein the probe tip surface is <about 5 mm.

16. The method according to claim 2, wherein the fluorescent label is a cyanine dye.

17. The method according to claim 2, wherein the chemi-luminescent label is ruthenium (II)tris-bipyridine or an acridinium ester.

18. The method according to claim 13, wherein the streptavidin is conjugated to a copolymer of sucrose and epichlorohydrin.

19. The method according to claim 18, wherein each copolymer carries about 20 to 30 streptavidins.

20. The method according to claim 19, wherein each copolymer further carries 2-3 Cy5 molecules per streptavidin, or 2-3 acridinium esters molecules per streptavidin.

\* \* \* \* \*